(12) United States Patent
Vermesh et al.

(10) Patent No.: US 10,064,653 B2
(45) Date of Patent: Sep. 4, 2018

(54) INTRAVASCULAR MAGNETIC WIRE FOR DETECTION, RETRIEVAL OR ELIMINATION OF DISEASE-ASSOCIATED BIOMARKERS AND TOXINS

(71) Applicant: The Board of Trustees of the Leland Stanford Junior University, Palo Alto, CA (US)

(72) Inventors: Ophir Vermesh, Palo Alto, CA (US); Sanjiv Sam Gambhir, Portola Valley, CA (US); Seung-min Park, Menlo Park, CA (US); Tianjia Jessie Ge, St. Louis, MO (US); Amin Aalipour, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 123 days.

(21) Appl. No.: 15/175,959

(22) Filed: Jun. 7, 2016

(65) Prior Publication Data
US 2016/0354116 A1  Dec. 8, 2016

Related U.S. Application Data

(60) Provisional application No. 62/172,648, filed on Jun. 8, 2015.

(51) Int. Cl.
*A61B 17/52* (2006.01)
*A61B 5/05* (2006.01)
(Continued)

(52) U.S. Cl.
CPC ............... *A61B 17/52* (2013.01); *A61B 5/05* (2013.01); *A61B 5/14546* (2013.01);
(Continued)

(58) Field of Classification Search
CPC ....... A61B 17/52; A61B 10/04; A61B 5/6851; A61B 5/05; A61B 5/14546; A61N 2/06
See application file for complete search history.

(56) References Cited

U.S. PATENT DOCUMENTS

| 5,921,244 A | 7/1999 | Chen |
| 7,553,625 B2 | 6/2009 | Hoon |

(Continued)

FOREIGN PATENT DOCUMENTS

| CA | 2831857 | 10/2012 |
| CN | 1554453 | 12/2004 |

(Continued)

*Primary Examiner* — Christine H Matthews
*Assistant Examiner* — Joshua D Lannu
(74) *Attorney, Agent, or Firm* — Lumen Patent Firm (57) ABSTRACT

A medical device and method for detection, retrieval or elimination of disease-associated toxins and biomarkers is provided. A plurality of magnets is arranged within a flexible sheath forming a flexible wire. The magnets are magnetically attached to each other, end-to-end, and arranged with their magnetic polarities alternating in direction. The magnetization direction of each of the magnets is orthogonal to the length axis of the flexible wire. The medical device is completely self-contained and does not require a bulky external field source able to maintain strong magnetic field gradients (100-10,000 T/m) along the wire, and at a radial distance (~1 mm) to attract magnetic particles throughout the entire vein diameter at a range of physiologic velocities (1-10 cm/sec). This technology is a major step forward for the clinical relevance of CTC analysis to personalized medicine and introduces a powerful generalizable strategy for enrichment of other rare blood biomarkers.

8 Claims, 12 Drawing Sheets

(51) Int. Cl.
  *A61B 5/00* (2006.01)
  *A61N 2/06* (2006.01)
  *A61B 10/04* (2006.01)
  *A61B 5/145* (2006.01)

(52) U.S. Cl.
  CPC .......... *A61B 5/6851* (2013.01); *A61B 10/04* (2013.01); *A61N 2/06* (2013.01)

(56) References Cited

U.S. PATENT DOCUMENTS

| | | |
|---|---|---|
| 8,999,650 B2 | 4/2015 | Flynn |
| 2002/0133115 A1* | 9/2002 | Gordon .................. A61L 29/16 604/96.01 |
| 2006/0025713 A1 | 2/2006 | Rosengart |
| 2006/0041182 A1 | 2/2006 | Forbes |
| 2006/0142630 A1 | 6/2006 | Meretei |
| 2009/0216320 A1 | 8/2009 | Levy |
| 2011/0117028 A1 | 5/2011 | Zharov |
| 2011/0218616 A1 | 9/2011 | Thomas |
| 2012/0149029 A1* | 6/2012 | Flynn ................. A61B 10/0233 435/7.1 |
| 2013/0261373 A1 | 10/2013 | Pison |
| 2014/0163664 A1* | 6/2014 | Goldsmith ....... A61B 17/00491 623/1.11 |
| 2015/0112299 A1 | 4/2015 | Forbes |

FOREIGN PATENT DOCUMENTS

| | | |
|---|---|---|
| WO | WO2006078994 | 7/2006 |
| WO | WO2007124016 | 11/2007 |
| WO | WO2009051734 | 4/2009 |
| WO | WO2013172966 | 11/2013 |

* cited by examiner

INTRAVASCULAR MAGNETIC WIRE FOR DETECTION, RETRIEVAL OR ELIMINATION OF DISEASE-ASSOCIATED BIOMARKERS AND TOXINS

CROSS-REFERENCE TO RELATED APPLICATIONS

This application claims priority from U.S. Provisional Patent Application 62/172,648 filed Jun. 8, 2015, which is incorporated herein by reference.

FIELD OF THE INVENTION

The invention relates to medical devices and methods for detection, retrieval, or elimination of disease-associated biomarkers and toxins from a blood vessel.

BACKGROUND OF THE INVENTION

Circulating tumor cells (CTCs) are cells that are shed by a tumor into the bloodstream and are key mediators of metastasis that can present key information about a patient's disease. CTCs are frequently present in patients with primary and recurrent cancer, and have been found in patients even before a primary tumor was detected by other diagnostic modalities. In addition to early detection, CTC analysis can provide molecular and genetic profiles of both a primary tumor and its metastases, thereby yielding a more complete molecular picture of disease than a tumor biopsy alone and providing a powerful tool for personalized medicine. While circulating tumor DNA (ctDNA) can also provide a genetic profile of cancer, it can be difficult to distinguish from abundant circulating non-tumor DNA and it does not provide the transcriptomic, proteomic, and drug susceptibility information afforded by CTC analysis. However, widespread clinical adoption of CTC analysis for early diagnosis of recurrence and guidance of treatment has been hindered by their rarity in the blood (often ~1-10 cells per milliliter). CTCs are typically detected at more advanced stages when tumor burden is no longer microscopic and is more difficult to treat, but even then, there are too few CTCs in a typical blood sample to conduct drug susceptibility testing, and the sampling is too sparse for molecular characterization to reflect the heterogeneity of the patient's disease. A larger, more representative CTC sample could be obtained by processing larger blood volumes, but there are practical limits to the amount of blood that can be drawn.

State-of-the-art CTC technologies cannot be easily scaled for higher throughput, for example, the CTC-Chip, FDA-approved CellSearch®, and microfluidic-based immunomagnetic separation technologies, while transformative, require hours to process a few milliliters of blood. Apheresis can process large blood volumes through an extracorporeal circuit, but requires a bulky, expensive setup, constrains patient mobility, and still necessitates considerable post-processing to isolate CTCs. Another method for sampling from large blood volumes introduces an antibody-coated stainless steel rod into a blood vessel for immunocapture of CTCs in flow, but the improvement in CTC yield over a standard blood draw is modest. This is likely due to the short residence time for CTCs to collide with and bind to the rod at normal blood flow velocities. In addition, cells in flow are unlikely to turn their trajectory toward the wire without an additional attractive force, as provided for example by a magnetic technique. Accordingly, new technology and strategies are therefore needed that can rapidly, safely, and effectively interrogate large blood volumes to achieve large-scale CTC enrichment for earlier disease detection and therapy selection.

SUMMARY OF THE INVENTION

A medical device and method is provided for detection, retrieval or elimination of disease-associated toxins and biomarkers such as cells, proteins, nucleic acids, circulating tumor DNA, or exosomes. A plurality of magnets is arranged within a flexible sheath forming a flexible wire. The magnets are magnetically attached to each other, end-to-end, and arranged with their magnetic polarities alternating in direction. In one example, the alternating end-to-end polarities alternate 180 degrees or they could alternate with a rotation from magnet to magnet at 45-180 degree increments. As an alternative to alternating individual magnets by 180 degrees, one can accomplish the same alternating polarity by, for example, rotating 180 smaller magnets by 1 degree or 4 magnets by 45 degrees. Therefore, for any magnetization angle (A) between adjacent magnets, the number (N) of magnets needed to cycle through 180 degrees is 180/A. In other words, the alternating end-to-end polarities could alternate with a rotation from magnet to magnet at 1-180 degree increments.

The magnetization direction of each of the magnets is orthogonal to the length axis of the flexible wire. There could be 10 to 1000 magnets forming the flexible wire with each of the magnets having a length in a range of 0.5 mm to 10 cm. In one example, the magnets are cylindrical magnets (rods) each having a diametric magnetization, however, the magnets do not have to be cylindrical. In case of cylindrical magnets they could have a diameter of 0.2 mm to 10 mm.

The medical device is dimensioned so that it can be introduced into a blood vessel, be kept as a self-contained device within the blood vessel and be retrieved from the blood vessel. The medical device is further dimensioned to allow blood flow along the length axis while being kept within the blood vessel.

The magnetic field along the length axis is sufficient to attract to the surface of the flexible wire superparamagnetic nanoparticles, which could bind themselves to the disease-associated toxins and biomarkers. The flexible wire is a self-contained device (i.e. without the use of an external magnetic source) could generate magnetic field gradients of 100 to 10,000 T/m. The magnets are displaceable from the sheath upon retrieving the medical device from the blood vessel for capturing and analysis of the disease-causing cells or the toxins.

Embodiments of the invention have several advantages. First, the magnetic wire is completely self-contained and does not require a bulky external field source. Second, the unique geometry of alternating-polarity magnetic units maintains strong magnetic field gradients (100-10,000 T/m) along the entire wire, and at a radial distance (~1 mm) that can attract magnetic particles throughout the entire vein diameter at a range of physiologic velocities (1-10 cm/sec). Third, the flexibility of the medical device, Magnetic Wire for Intravascular Retrieval and Enrichment (MagWIRE), allows it to be easily guided to and retrieved from distant sites within the body, just like an interventional guidewire, without trauma to the vessel. Fourth, the length of the MagWIRE can be increased to achieve greater capture surface area and improved capture in higher flow-rate vessels.

BRIEF DESCRIPTION OF THE DRAWINGS

FIG. 1 shows an overview according to an exemplary embodiment of the invention the MagWIRE device and method for detection, retrieval or elimination of disease-associated toxins and biomarkers. Insert (a) shows antibody-coated magnetic particles (MPs) injected and binding rare analytes in the blood, for example circulating tumor cells (CTCs) (Ab is antibody). Insert (b) shows the flexible MagWIRE introduced through an IV catheter, collecting and enriching MP-bound cells on the wire as the entire blood volume circulates past (approximately one hour). Insert (c) shows the MagWIRE being removed from the vein and the magnets are displaced, leaving the captured cells on the sheath for elution, ex vivo cell culture, and downstream molecular analysis.

FIGS. 2A-C show according to an exemplary embodiment of the invention numerical simulations of the magnetic properties of a MagWIRE segment.

FIGS. 3A-F show experimental results according to an exemplary embodiment of the invention.

FIG. 5 shows an exploded view of the MagWIRE according to an exemplary embodiment of the invention. A plurality of magnets (here shown two, 510, 520) are arranged within flexible sheath 530 forming a flexible wire 500. The magnets are magnetically attached end-to-end (i.e. they are not separated from each other) and arranged with their magnetic polarities alternating in direction (P1 and P2 are alternating polarities). The magnetization direction of each of the magnets is orthogonal to the length axis of the flexible wire.

DETAILED DESCRIPTION

Figure 1:
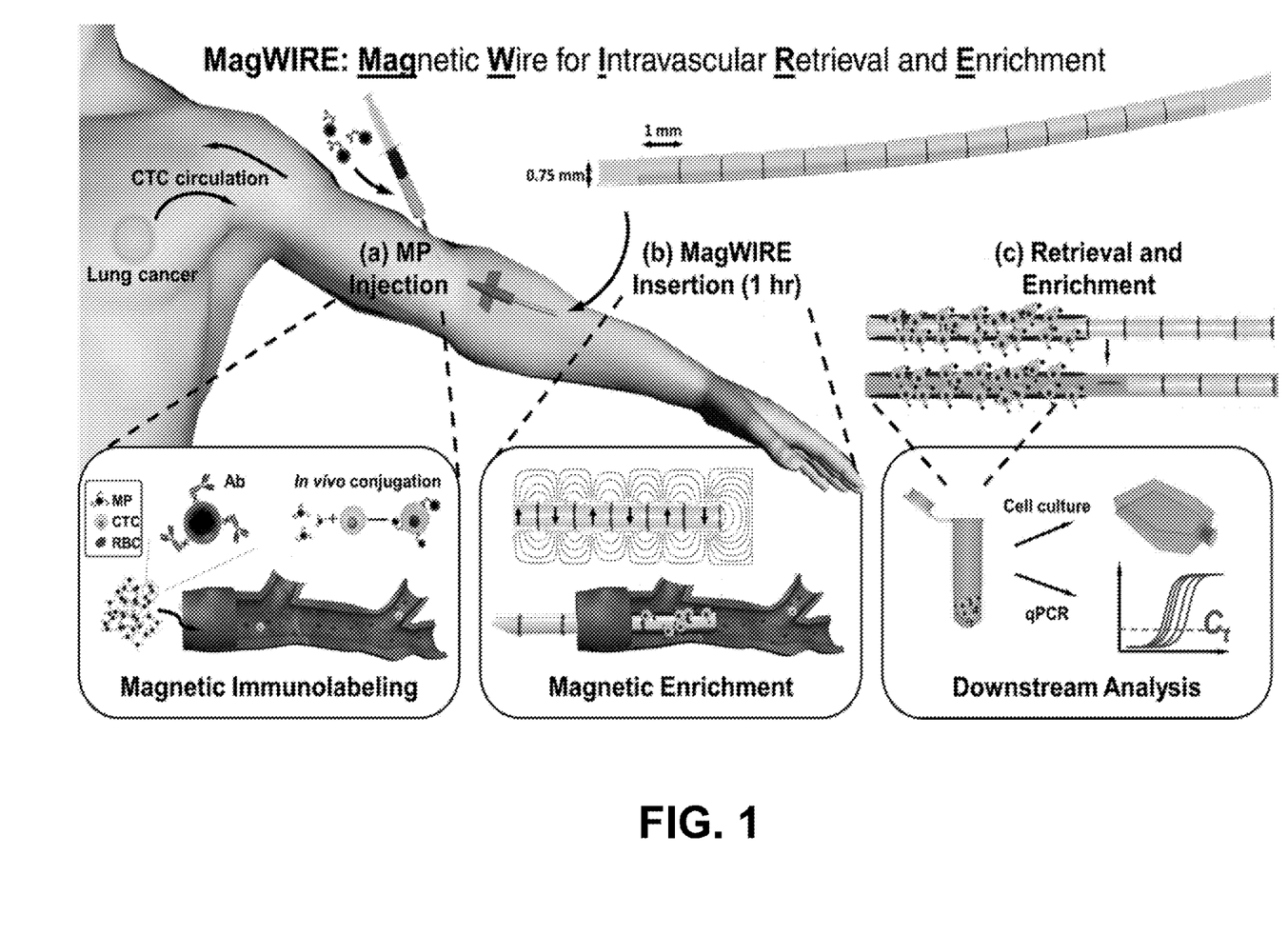
Figure 5:
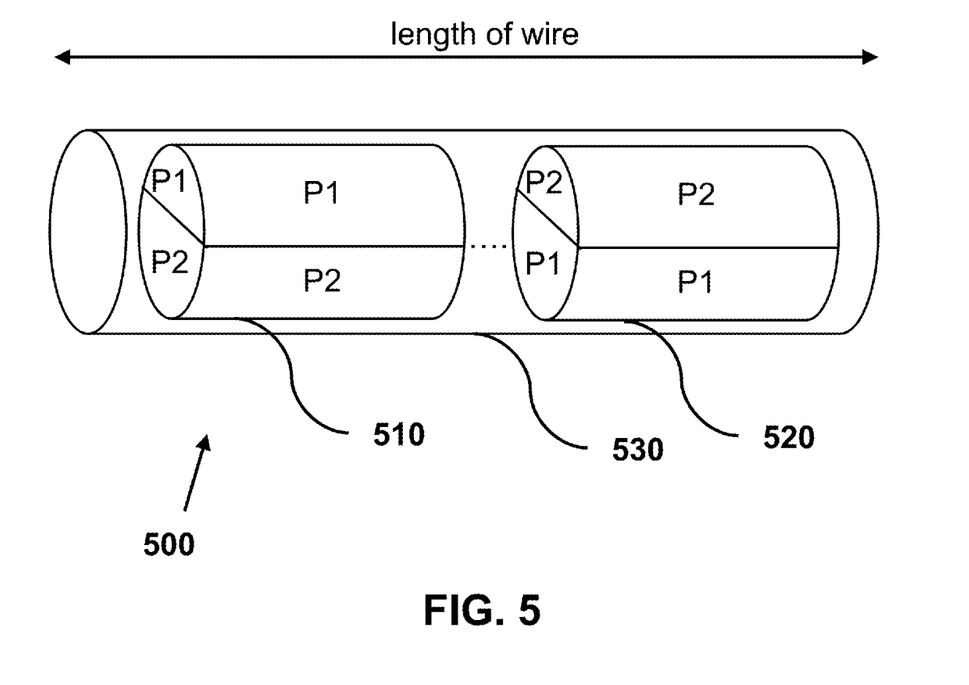

With this invention we provide a device and method for in vivo magnetic enrichment of rare biomarkers such as CTCs. The device is herein referred as the MagWIRE, which stands for Magnetic Wire for Intravascular Retrieval and Enrichment (FIGS. 1 and 5). The MagWIRE is a magnetic wire encased in a biocompatible plastic sheath. Its small diameter and flexibility allow it to be easily introduced into and retrieved from a blood vessel without causing occlusion or trauma, similar to medical guidewires that are used in vascular interventional procedures.

The design of the MagWIRE maximizes the surrounding volume from which targets can be magnetically captured by achieving high local field gradients along its entire length without relying on an external magnetic field source.

FIG. 1 shows an overview of the MagWIRE device and method for detection, retrieval or elimination of disease-associated toxins and biomarkers. A patient is injected with antibody-coated magnetic particles (MPs), similar to FDA-approved Feraheme®. After allowing the MPs to circulate and immunolabel their target, the MagWIRE is inserted into a superficial vein in the arm and captures passing MP-bound biomarkers. Within an hour, about 5 liters (the equivalent of the entire adult blood volume) has circulated through for example a 2-3-mm-diameter human vein, allowing most of the patient's blood volume to be sampled.

In principle, after MP injection and wire placement, the patient could move freely and return an hour later for removal of the wire. The magnets can then be displaced from the MagWIRE sheath to elute the bound targets into buffer for downstream analysis.

To illustrate the gains achievable by sampling from large volumes, consider the total number of CTCs (N) that can be captured by the MagWIRE, as described by the equation: N=C×V×E (Equation 1), relating to CTC concentration (C), total blood volume processed (V), and percentage capture efficiency (E). At a CTC concentration of 1 cell/mL, a 5-10 mL blood sample would contain only about 5-10 CTCs. By comparison, if sufficient time is allotted for 5 liters of blood to circulate past the MagWIRE, then even at a capture efficiency of only 5%, the total number of CTCs captured would be 250 (N=0.05*1*5000), a 25-50 fold improvement.

We demonstrated the MagWIRE system's capability for rapid CTC labeling and capture both in vitro in a closed-loop circulation system as well as in vivo in a porcine model. Captured CTCs can be genomically characterized and remain viable for cell culture. We describe the design of the MagWIRE and its potential in different use situations, such as targeting of different rare biomarkers.

MagWIRE Design

Figure 2A:
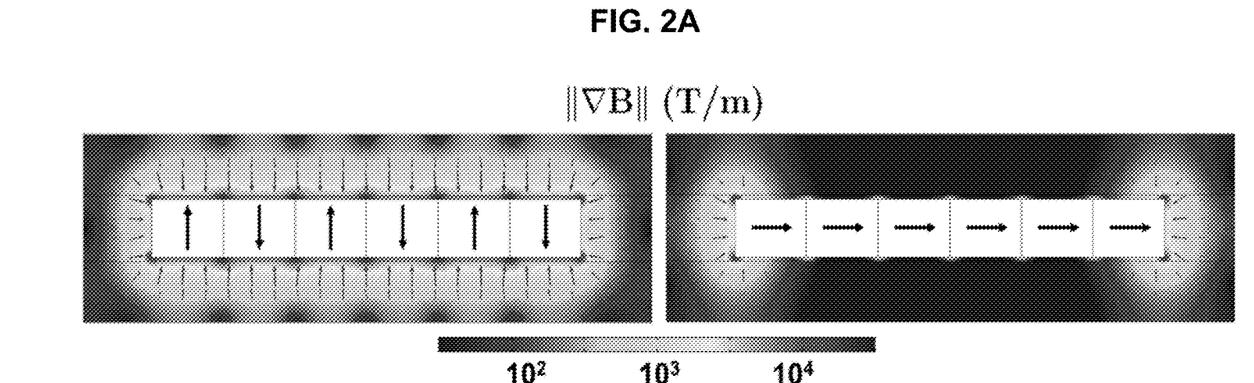
FIG. 2A shows a comparison of magnetic field gradient ∇B between different magnetic orientations (black arrows shown within the magnets point north). The alternating orientation (left image in FIG. 2A) generates high gradients and magnetic forces ('red' arrows shown outside the magnets, scaled logarithmically) to attract magnetic particles along the entire length, while the axial orientation (right image in FIG. 2A) only localizes gradient and force at the ends.

A particle in a magnetic field experiences a magnetic force F=m·∇B (Equation 2), wherein m is the magnetic moment of the particle, and ∇B is the magnetic field gradient. The MagWIRE produces a high magnetic field gradient, and thus large attractive force, through its specialized configuration. In one example, the functional magnetic part of the MagWIRE has a plurality of small, cylindrical N50 neodymium magnets. For example, 60 units or magnets can be used totaling 6 cm in length. Importantly, each unit is magnetized across its diameter (diametrically magnetized, FIG. 1 and FIG. 5) and the units are arranged end-to-end within the sheath such that their magnetic polarities alternate. As a result, the surface magnetic flux density B (~1 T) and field gradient ∇B (FIG. 2A, left) remain relatively uniform along the entire length of the wire.

Figure 2B:
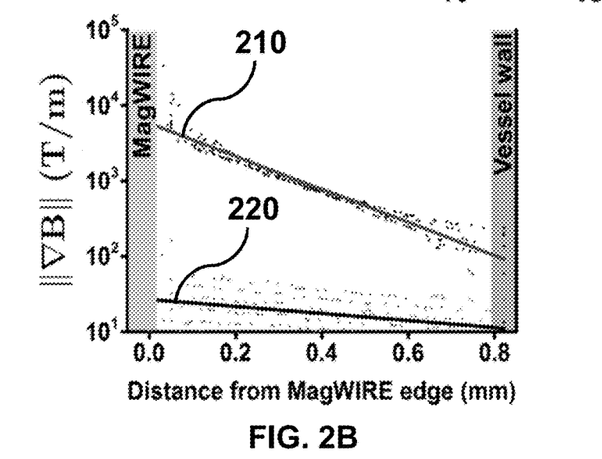
FIG. 2B shows the gradient decays radially outward from the MagWIRE edge. Multiple points are sampled along the length of the magnet (dots), and the mean gradient is shown (solid line). The alternating polarity configuration 210 outperforms the axial configuration 220 by orders of magnitude.

Compared to a magnetic wire with axial polarity, which localizes field gradients only at the ends (FIG. 2A, right), the MagWIRE maximizes the volume of high gradient and efficient cell capture. The local magnetic gradient approaches ∇B=10,000 T/m close to the surface of a 0.75 mm MagWIRE, 1000 T/m halfway between the MagWIRE and the wall of a vessel 2.4 mm in diameter, and remains >100 T/m at the vessel wall (FIG. 2B). These values are in contrast to gradients of 1-10 T/m achieved by other magnetic separation devices.

Figure 2C:
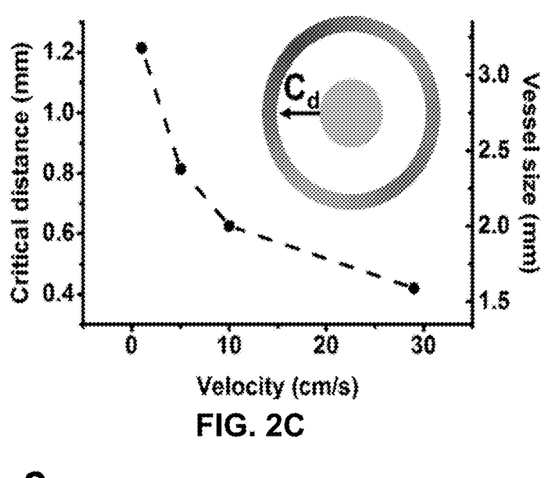
FIG. 2C shows the 'critical' distance ($C_d$) is the radial distance from the MagWIRE at which 90% of MP-labeled cells can be captured in blood, when cells are labeled with 100 MPs. The corresponding vessel size for a 0.75 mm MagWIRE is shown on the right axis.

As a particle is attracted to the MagWIRE by the magnetic force $F_m$, there is an opposing fluidic drag force described by $F_d$=6πaηv (Equation 3), where η is viscosity of the medium, a is particle diameter, and v is the velocity at which the particle approaches the wire. To be captured, a particle must traverse the radial distance to the wire surface before the blood flow carries it past the wire's length. For different blood flow velocities, we performed numerical simulations in COMSOL to determine the maximal reach of the MagWIRE, or the 'critical' distance from the wire at which 90% of MP-labeled cells are captured from flow assuming each cell is labeled with 100 MP (FIG. 2C). A 0.75 mm diameter MagWIRE has a critical distance of approximately 1 mm at physiologically relevant flow rates of 1-10 cm/s. Thus, it is thin enough to fit within a 2-3 mm diameter vein without obstructing flow, but still large enough to attract distant cells near the vessel walls.

Magnetic Enrichment of CTCs in a Closed-Loop System

Figure 3A:
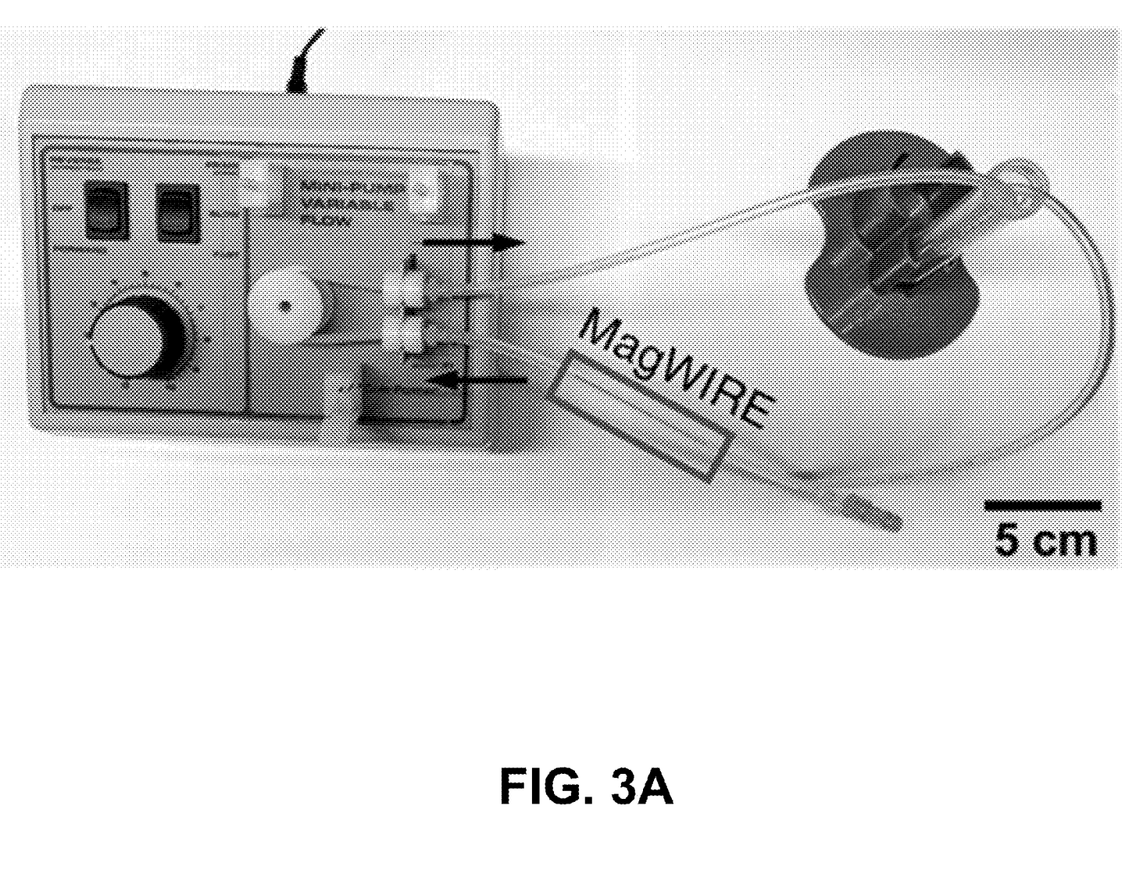
FIG. 3A shows the MagWIRE being tested in a closed loop circulation system consisting of a peristaltic pump, tubing, and a reservoir.

To assess the feasibility of intravascular magnetic enrichment, we modeled blood flow with a closed-loop circulation setup (FIG. 3A). Our tubing inner diameter of 2.38 mm and flow rate of 2 cm/s reflect physiologically relevant flows and shear stresses in superficial veins like the cephalic vein in the arm. To model CTC capture, we targeted H1650 lung cancer cells with 1-μm iron oxide superparamagnetic particles (Dynabeads) coated with antibodies against the common CTC surface marker Epithelial Cell Adhesion Molecule (EpCAM), which is expressed on CTCs of epithelial origin but not on blood cells, allowing selective enrichment. However, other CTC markers, such as E-cadherin, N-cadherin, or mesenchymal markers could also be targeted with this method.

Figure 3B:
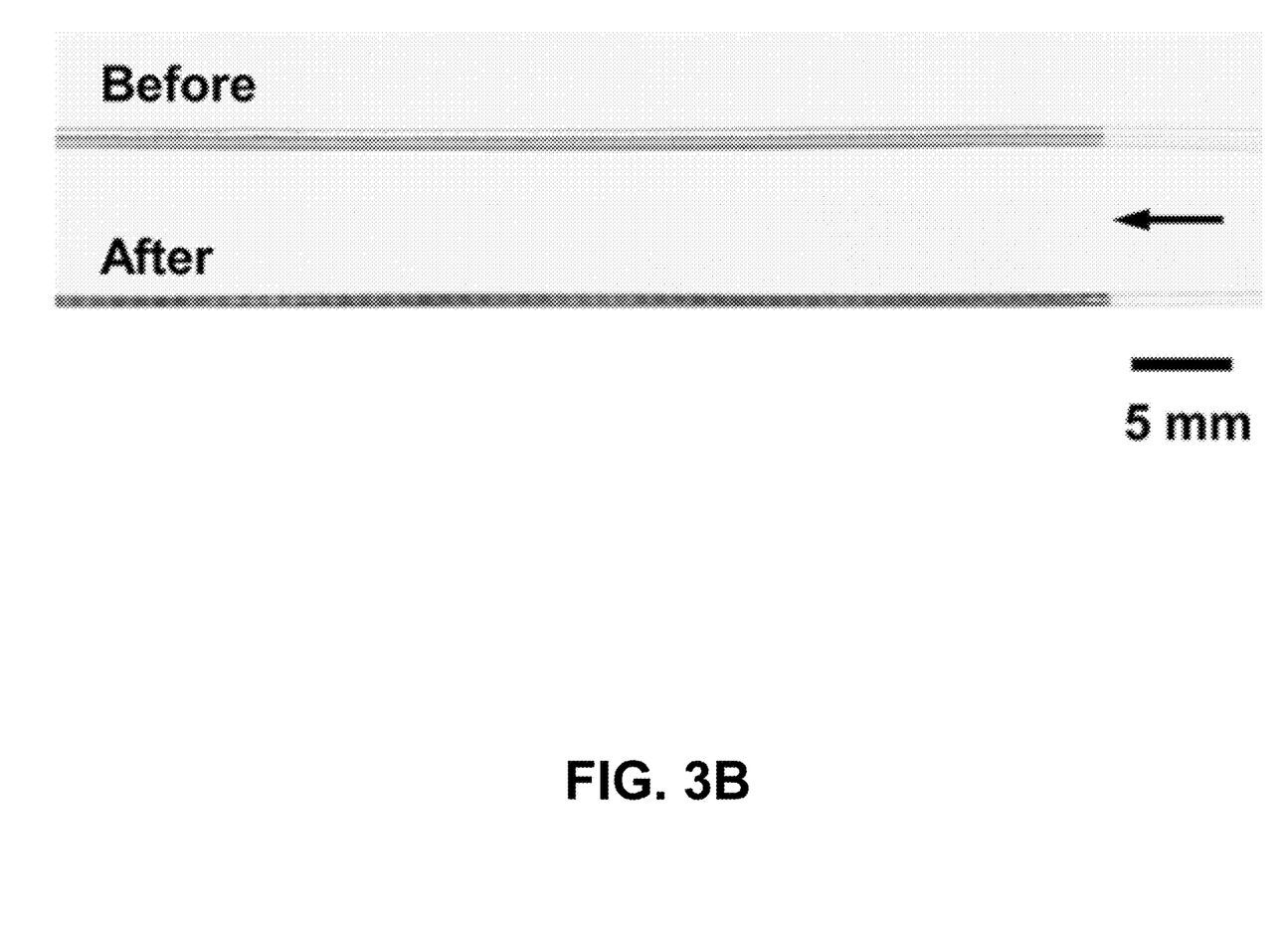
FIG. 3B shows, after retrieval, the MagWIRE has been coated with MPs. The arrow points in direction of fluid flow for all images.
Figure 3C:
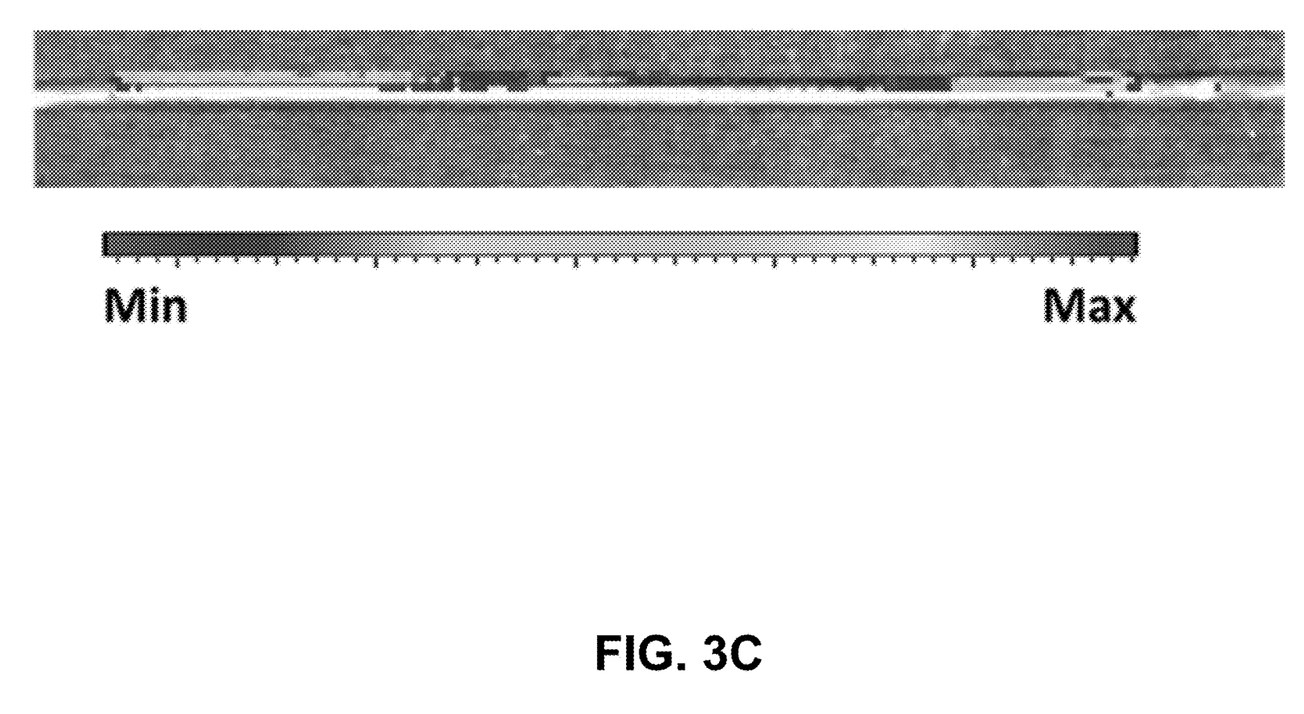
FIG. 3C shows labeling the cells with CellTracker Orange, the captured cells can be fluorescently visualized. Macroscopic imaging shows that the entire wire is coated with cells.
Figure 3D:
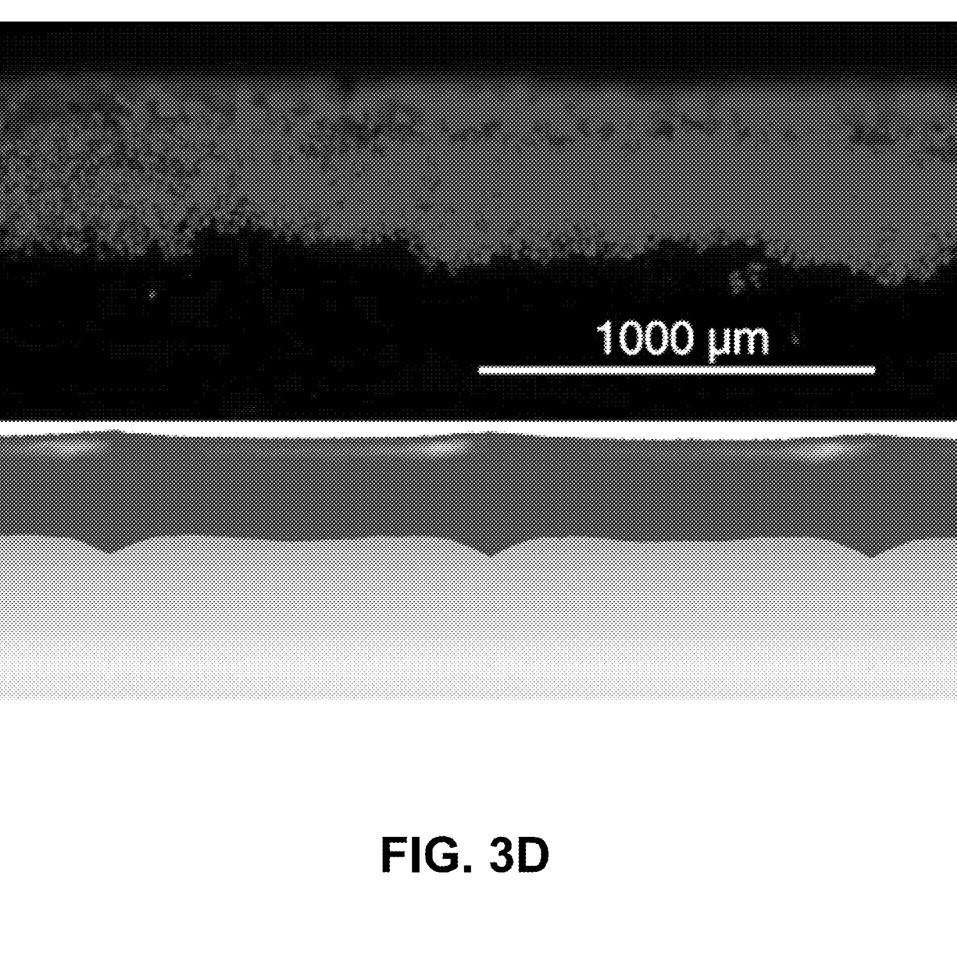
FIG. 3D shows microscopy results indicating that the distribution of cells (top) matches magnetic energy density ($B^2$) simulation results (bottom). Capture efficiencies for both pre-labeled and post-labeled cells under continuous circulation conditions are shown for buffer and blood (FIG. 3E).

Some of our experiments aimed to assess the capture efficiencies of model CTCs in "ideal" conditions where the cells are prelabeled with MPs, and then spiked into a closed-loop system of circulating buffer. The MagWIRE was introduced into circulation for 10 minutes, and then removed for elution of enriched cells. Capture efficiency was calculated as the percentage of cells introduced into the system that were recovered on the MagWIRE. As expected, the MagWIRE was coated along its entire length by MPs (FIG. 3B), and fluorescent labeling of the cells demonstrated a similar distribution (FIG. 3C). As particles and cells are attracted to the MagWIRE, one expects that they will deposit according to surfaces of constant magnetic energy $$\frac{B^2}{2\mu_0},$$

where $\mu_0$ is the vacuum permeability of free space. Indeed, microscopy confirms that the pattern of cell deposition matches the simulation (FIG. 3D).

Since we introduced low cell concentrations (10-1,000 cells/mL) that are within the range of reported physiologic CTC concentrations, conventional hemocytometry was insufficiently sensitive for cell enumeration. Instead, we determined capture efficiencies by extracting genomic DNA and performing qPCR with a standard curve of known cell numbers. Additionally, because genomic characterization of CTCs is critical to their clinical utility, we targeted the EGFR exon 19 deletion (ΔE746-A750), which is common in non-small cell lung cancer, with a mutation specific hydrolysis qPCR probe. Our method of magnetic labeling does not interfere with extraction of genomic information from CTCs, allowing us to accurately quantify small numbers of captured cells.

Figure 3E:
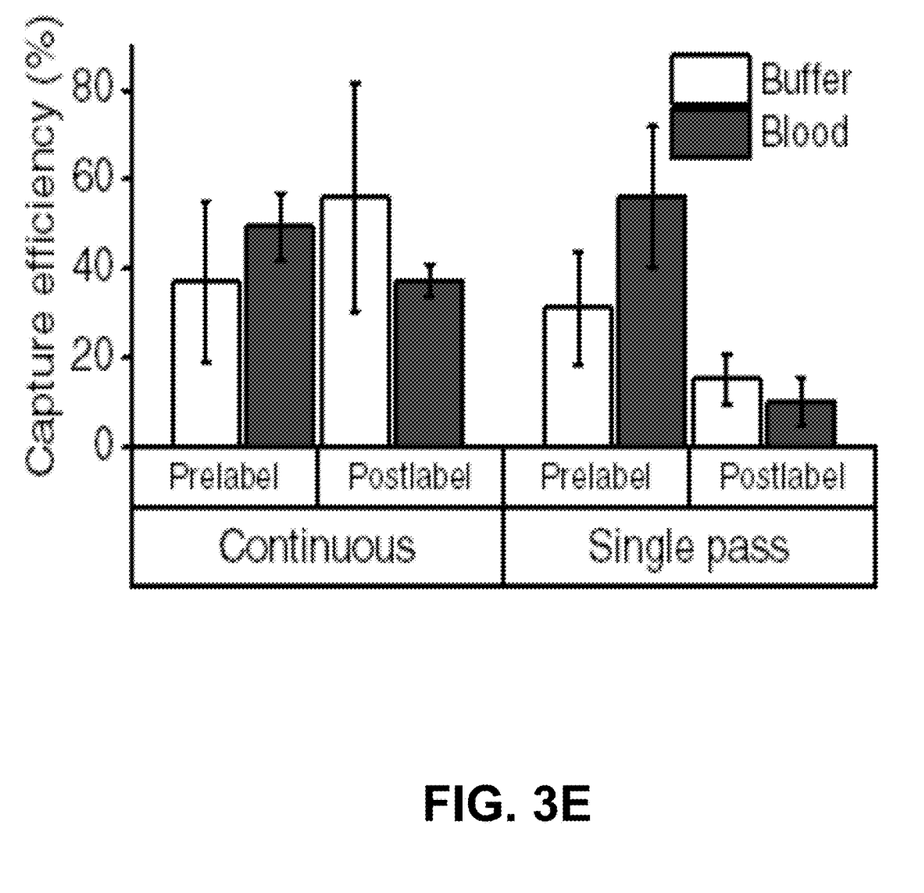

Using this method of quantitation, we captured an average of 37%+/−18% (25%-58%) of pre-labeled cells spiked at concentrations of 10, 100, and 1,000 cells/mL, confirming that magnetically labeled cells can be enriched on a magnetic wire in physiologically relevant conditions (FIG. 3E). Importantly, the EGFR exon 19 deletion was detected in enriched cells from all experiments, even at concentrations of 10 cells/mL. Capture efficiencies exhibited high variance among the different cell numbers introduced, likely due to high stochasticity when fewer cells are involved. Notably, only 0.1% of cells were captured with a non-magnetic wire at the highest cell concentration tested, suggesting that non-specific binding of cells to the plastic sheath is negligible. Additionally, attempted capture of PCS-201 fibroblasts, a human cell line that does not express EpCAM, also yielded capture efficiencies of only 0.6% at 1,000 cells/mL, confirming that MP labeling is specific to EpCAM-expressing cells. This binding specificity is of particular significance given the rarity of CTCs compared to the high background of 'normal' cells in human blood.

While encouraged by our capture results for pre-labeled cells, capture of CTCs in vivo requires MPs to bind cells under flow conditions. We therefore proceeded to closed-loop experiments in which we first circulated cells within the system and afterwards introduced anti-EpCAM MPs into the flow. The MPs were given time to "post-label" cells in flow prior to introduction of the magnetic wire. Cells captured by the wire were isolated and quantified as previously described. Even in this post-labeled condition, capture efficiencies were on average 55.86%+/−25.47% (40.52%-85.27%) across all cell numbers introduced in buffer, confirming that cell-MP binding is possible under flow conditions (FIG. 3E). Furthermore, 97% of introduced MPs were recaptured by the wire (not shown).

Figure 3F:
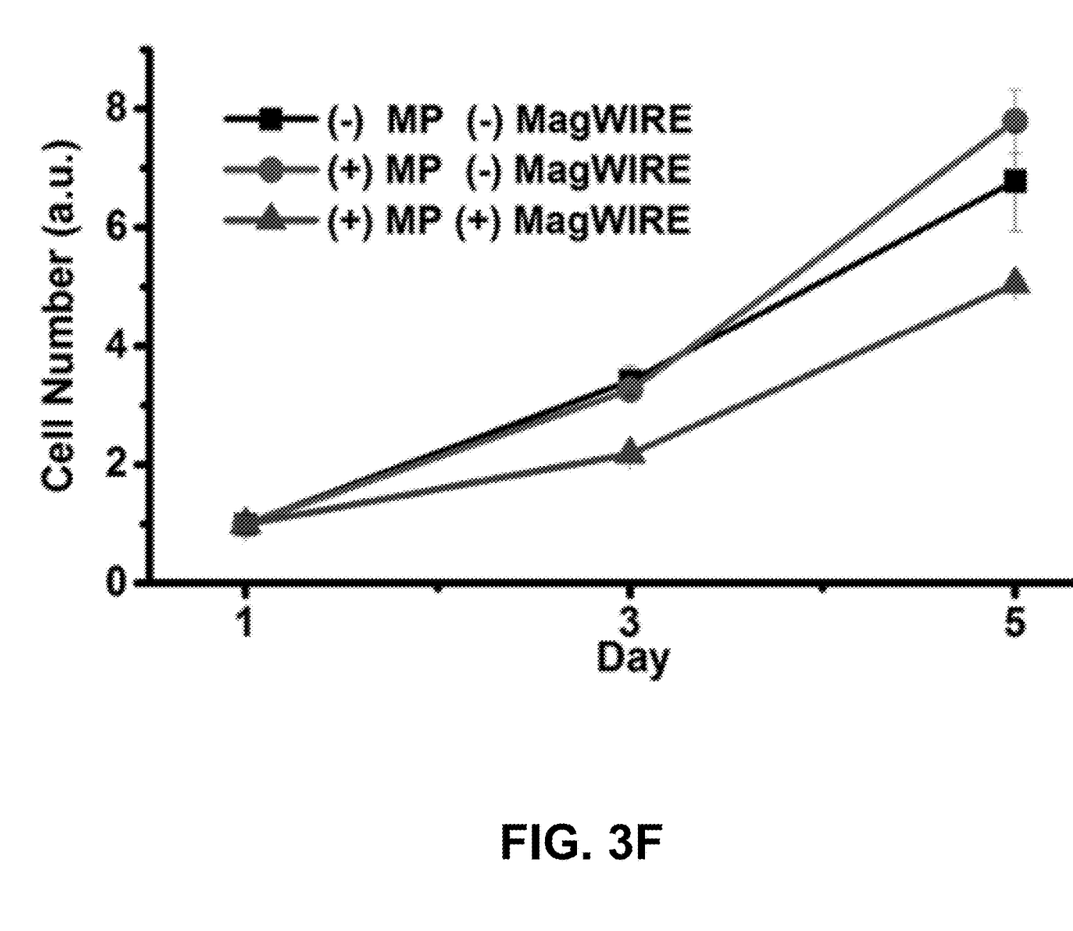
FIG. 3F shows that the captured cells remain viable for cell culture, proliferating over a period of 5 days (a.u. is arbitrary units).

Our method of magnetic enrichment was also effective when closed loop experiments were performed in whole human blood from healthy donors. Even though blood is 3-4 times more viscous than water, capture efficiencies were similar—49.34%+/−7.63% (33.55%-54.73%) for prelabeled cells, and 37%+/−y % for postlabeled cells. This demonstrates that the strong magnetic force of the MagWIRE allows it to capture similar numbers of cells in blood compared to buffer despite the much higher viscous drag of blood. Additionally, cells that had been labeled and captured in blood remained viable for cell culture after elution (FIG. 3F).

Since capture efficiencies were similar in both the pre-labeled and post-labeled setups across a range of cell concentrations, it appears that cell capture in this circulating setup is not limited by labeling in flow or by the Mag- WIRE's capabilities. Rather, the observed limits in capture efficiency are likely due to an inherent property of the cells, such as the level of EpCAM expression. Flow cytometry analysis of H1650 cells indicated that EpCAM expression varies over nearly three orders of magnitude (not shown), which could contribute to the variation in MP cell labeling. Microscopy of pre-labeled cells also reflected this variation, with noticeable differences in the degree of MP binding from cell to cell (not shown).

Rapid Localized in vivo Cell Labeling and Magnetic Capture

Figure 4A:
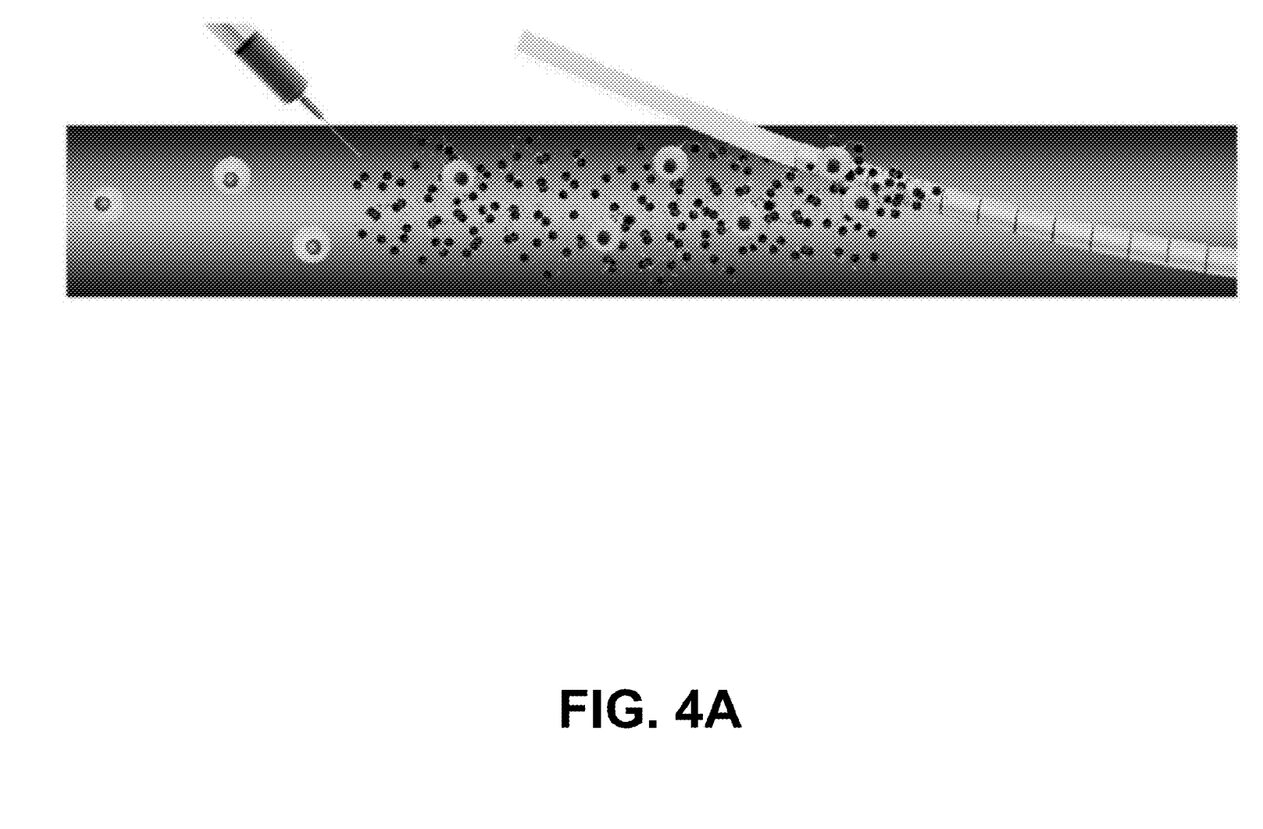
FIGS. 4A-C shows according to an exemplary embodiment of the invention the MagWIRE tested in a single flow set-up to evaluate the performance of rapid labeling and localized enrichment (FIG. 4A) in buffer and blood (see also FIG. 3E). This methodology was then evaluated in a porcine model, where the MagWIRE was inserted into the auricular vein, and H1650 cells and anti-EpCAM MPs were infused in the same vein upstream of the MagWIRE (FIG. 4B, top). Fluoroscopy demonstrates that the MagWIRE (red arrow, 410) advances through a tortuous vessel (FIG. 4B, bottom). Capture efficiencies in the porcine model are shown for infusions of 10,000 pre-labeled cells, 2,500-10,000 post-labeled cells, and for a non-magnetic wire (FIG. 4C).

While the MagWIRE technology can be generalized for many rare blood biomarkers, our device and method captures circulating tumor cells with a unique approach. While labeled biomarkers must pass by the MagWIRE to be captured, there exist two approaches to labeling. In one case, small MPs with a long circulation half-life can be administered as a single large bolus to bind to biomarkers throughout the blood before inserting the MagWIRE to collect the magnetically labeled biomarkers. Alternatively, if it were possible to rapidly label targets on the order of seconds as they traverse through an area of high MP concentration, then we could both magnetically label and capture biomarkers within the same vein (FIG. 4A). In practice, a patient would receive a steady infusion of MPs immediately upstream of the MagWIRE over the course of ~1 hour, over which time nearly the entire blood volume would pass through an area of high MP concentration for rapid biomarker labeling and downstream capture. The infusion can be delivered through a portable syringe pump to maintain mobility during the procedure.

The advantages of both labeling and capturing CTCs in the same vein are numerous. CTCs already have a short half-life on the order of minutes to a few hours due to capillary filtration and apoptosis. Systemic labeling of cells would be inefficient, as most of the labeled CTCs would be cleared before reaching the MagWIRE. A localized labeling strategy, on the other hand, limits MP dose by labeling only those CTCs that will be flowing past the MagWIRE. This strategy also allows us to use larger MPs for increased cell capture. The half-life of circulating MPs is inversely correlated with their size due to rapid clearance of large particles (>100 nm) by the reticuloendothelial system, requiring the use of smaller, less magnetizable MPs for systemic labeling. Since our approach does not rely on long circulation times, but instead captures MPs and MP-labeled cells on a single pass before they enter the systemic circulation, we can use large (1 um) MPs for CTC capture. The high magnetic gradients generated by the MagWIRE lead to the capture of >96% of MPs on the first pass in vitro (compared to the >98% captured in the continuous flow experiments, limiting systemic exposure and any potential toxicity in this localized enrichment method.

To determine whether a cell could be both labeled and captured within a single stream, we modified the closed-loop system into a single flow system with separate inlet and outlet reservoirs. The capture efficiency for prelabeled cells on a single passage by the MagWIRE averaged 31%+/−13% (22%-46%) (FIG. 3E). Pre-labeled cells in a continuous flow system were captured with an average efficiency of 37%, suggesting that a significant number of labeled cells are caught during their first interaction with the wire's magnetic fields. Similarly, 96% of beads were captured on a single pass.

Postlabeled experiments in the single flow system were conducted by infusing 1 mg of MP over the course of 1 min as a known quantity of cells flowed past. The functional end of the MagWIRE was located 15 cm downstream of the MP infusion site, such that cells had only 10 seconds for labeling. In buffer experiments, we show that an average of 15%+/−6% (9%-20%) of cells are both labeled and caught by the implanted wire on a single pass, indicating the feasibility of rapid CTC labeling as they traverse through a region of high MP concentration. (FIG. 3E). Microscopic inspection of the captured cells revealed high MP labeling (in contrast to uncaptured cells), confirming the specificity of capture (not shown). The MagWIRE again demonstrated similar capture efficiencies in whole blood (56%+/−16% (39%-70%) for prelabeled cells, 10%+/−5% (6%-16%) for postlabeled) (FIG. 3E). As previously mentioned, the utility of this technology derives not from high capture efficiencies, but from integrating capture of CTCs over time and volume to achieve a manyfold increase in CTC yield (Equation 1).

CTC Capture in an in vivo Porcine Model

Figure 4B:
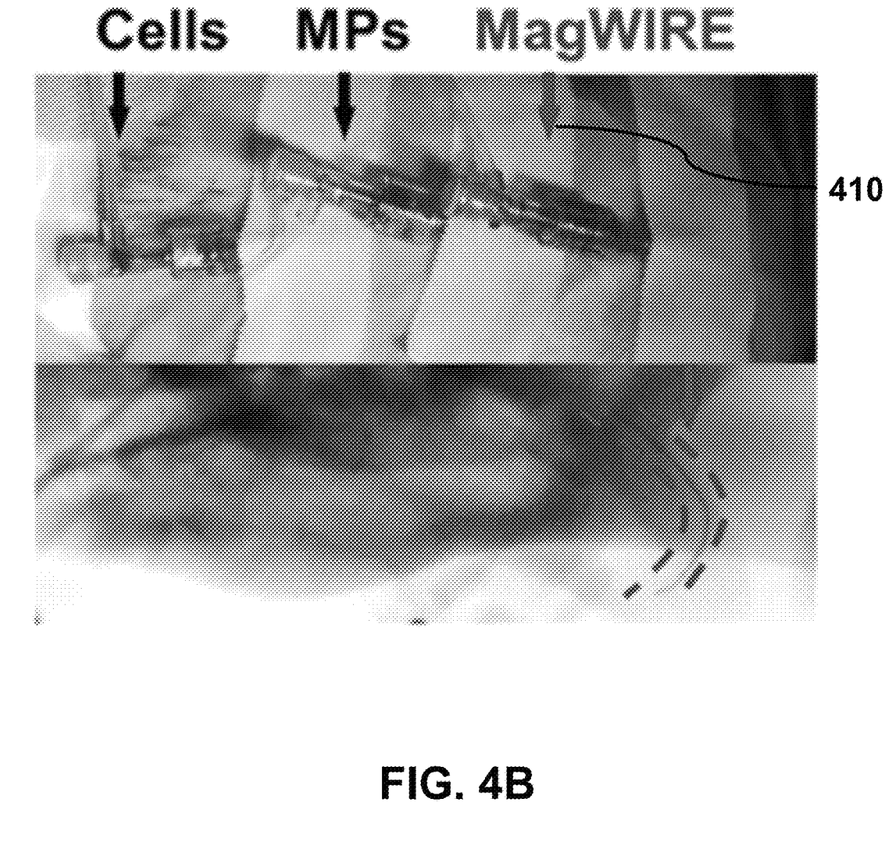

To demonstrate the translational potential of MagWIRE, we implemented the local enrichment method of CTC capture in a live Yorkshire pig. The Yorkshire auricular vein is similar in accessibility and size to human cephalic and basilic veins, making it an ideal choice for an in vivo proof of principle. Given the technical challenges of generating endogenous CTCs in a porcine model by mutagenesis, we introduced exogenous cancer cells in the auricular vein in quantities that are representative of human CTC concentrations. The capture experiments involved three catheters in the same vein spaced 5 cm apart from one another, such that the distal and middle catheters were used to simultaneously infuse exogenous CTCs and MPs, respectively, while the most proximal catheter provided intravenous access for the MagWIRE to capture MPs and MP-labeled cells (FIG. 4B).

Figure 4C:
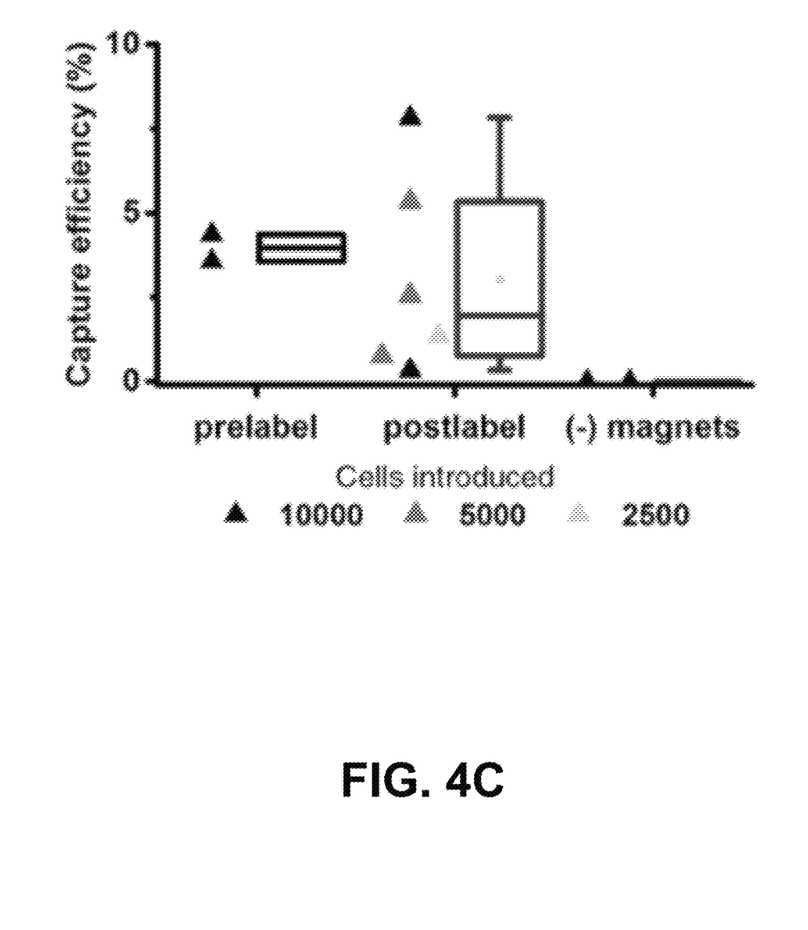

We infused MPs and between 2,500 to 10,000 cells over the course of a minute. Estimating an average blood flow of 10 mL/min in the auricular vein, an infusion of 2,500 cells over 1 minute corresponds to a local concentration of 250 cells/mL. Visual inspection of the removed MagWIRE showed noticeable coating by MPs, confirming that particles can be magnetically captured under in vivo flow conditions in real vasculature, and remain bound even during wire removal from a tortuous vessel (FIG. 4B). We captured cells with efficiencies ranging from a low of 1% for 2,500 cells to 8% for 10,000 cells (corresponding to 1,000 cells/mL) (FIG. 4C), which was ~50% of efficiencies seen in vitro. A non-magnetic wire captured no cells, again confirming capture specificity. Based on Equation 1, a 1-8% capture efficiency corresponds to a 10-80 fold enrichment over a 5 mL blood draw.

While these results translate to dramatic increases in CTC enrichment, they may in fact still underestimate the capture efficiencies attainable in human use. For one, the porcine ear is a highly vascularized structure with numerous collateral vessels that are visible by fluoroscopy, meaning that not all beads and cells injected in the selected vein necessarily pass by the magnetic wire. While 96% of MPs are captured in vitro, only about 34% on average are captured in vivo despite a similar flow velocity and vessel size, suggesting that as many as two-thirds of injected MPs and cells are escaping through these collaterals. Thus, only a third of injected cells may be flowing past the wire, such that actual capture efficiencies are effectively 3-fold higher. This, in part, could explain the lower capture efficiencies in vivo for even pre-labeled cells. In addition, the iodinated contrast agent used to visualize the MagWIRE by fluoroscopy prior to each trial is viscous and sticky, and may have accumulated within the vein after several trials, causing cell and MP adhesion to the vessel wall. Moreover, our setup requires an additional catheter for exogenous CTC delivery, not needed in the case of endogenous CTC capture, which may contribute to vein irritation and clamping that could promote collateral escape of injected cells. While our trials exhibited substantial variability, this is at least in part due to short (1 minute) enrichment times.

In the human case, enrichment would likely take place over the course of 30-60 minutes to sample the entire blood volume and this added integration time could reduce capture variability. Lastly, we performed multiple experiments within each vein, resulting in a level of irritation that would not occur in a human subject, where the MagWIRE would be introduced and removed only once.

Methods

MagWIRE Construction

In one example, cylindrical N50 grade neodymium magnets measuring 0.75 mm in diameter by 1 mm in length, magnetized across the diameter were inserted into PTFE tubing with an inner diameter (ID) of 0.81 mm and wall thickness of 38.1 µm. Non-magnetic control wires having a stainless steel rod of similar diameter were inserted into the PTFE tubing. The steel rod is to provide a non-magnetic control while still having something metal in the PTFE tubing. The stainless steel rod was part of a guidewire which is stated to be of similar physical properties to the MagWIRE.

After the experiments, the MagWIRE was removed and the magnets were pushed out of the end of the tubing using a thin stainless steel rod. The tubing was either placed into a 1.5 mL Eppendorf tube for DNA extraction or a 15 mL Falcon tube for elution for cell culture.

What is claimed is:

1. A medical device for detection, retrieval or elimination of disease-associated toxins and biomarkers, comprising:
    a plurality of magnets arranged within a flexible sheath forming a flexible wire, the flexible wire having a surface and a length axis,
    wherein the magnets are magnetically attached end-to-end and arranged with their magnetic polarities alternating in direction, each of the magnets having a magnetization direction;
    wherein the magnetization direction of each of the magnets is orthogonal to the length axis of the flexible wire;
    wherein the medical device is dimensioned to be introduced into a blood vessel, to be kept as a self-contained device within the blood vessel and to be retrieved from the blood vessel;
    wherein the medical device is dimensioned to allow blood flow along the length axis while being kept within the blood vessel;
    wherein a magnetic field along the length axis is sufficient to attract to the surface of the flexible wire superparamagnetic nanoparticles which could bind themselves to the disease-associated toxins and biomarkers;
    wherein the magnets are displaceable from the sheath upon retrieving the medical device from the blood vessel for capturing and analysis of disease-causing cells, the biomarkers or the toxins; and
    wherein the self-containing device operates without an external magnetic source.

2. The medical device as set forth in claim 1, wherein the magnets are cylindrical magnets each having a diametric magnetization.

3. The medical device as set forth in claim 1, wherein the magnets are cylindrical magnets having a diameter of 0.2 mm to 10 mm.

4. The medical device as set forth in claim 1, wherein the alternating polarities alternate 180 degrees or alternate with a rotation from magnet to magnet at 45-180 degree increments.

5. The medical device as set forth in claim 1, wherein each of the plurality of magnets has a length in a range of 0.5 mm to 10 cm.

6. The medical device as set forth in claim 1, wherein the medical device contains 10 to 1000 magnets.

7. The medical device as set forth in claim 1, wherein the flexible wire generates magnetic field gradients of 100 to 10,000 T/m.

8. The medical device as set forth in claim 1, wherein the disease-associated toxins and biomarkers are cells, proteins, nucleic acids, circulating tumor DNA, or exosomes.

* * * * *